United States Patent [19]

Beswick

[11] 4,085,146

[45] Apr. 18, 1978

[54] PROCESS FOR PREPARING O-HYDROXYARYLALDEHYDES

[75] Inventor: Geoffrey Ernest Beswick, Manchester, England

[73] Assignee: Imperial Chemical Industries Limited, London, England

[21] Appl. No.: 744,279

[22] Filed: Nov. 23, 1976

[30] Foreign Application Priority Data

Dec. 15, 1975 United Kingdom ............... 51286/75

[51] Int. Cl.$^2$ ............................................. C07C 45/16
[52] U.S. Cl. .................................. 260/600 R; 260/571
[58] Field of Search ...................................... 260/600 R

[56] References Cited

U.S. PATENT DOCUMENTS

| 1,345,649 | 7/1920 | Weiss ..................................... 260/600 |
| 1,783,584 | 12/1930 | Reddelien et al. ................... 260/600 |
| 2,576,064 | 11/1951 | Britton et al. ......................... 260/600 |
| 2,576,065 | 11/1951 | Britton et al. ......................... 260/600 |
| 3,173,956 | 3/1965 | Grinstead ............................. 260/600 |

OTHER PUBLICATIONS

Walker, Formaldehyde (1964) pp. 319-321.

*Primary Examiner*—Bernard Helfin
*Attorney, Agent, or Firm*—Cushman, Darby & Cushman

[57] ABSTRACT

A process for the manufacture of o-hydroxyarylaldehydes which comprises the steps of (1) oxidizing a 2-arylaminomethylphenol, optionally substituted in the phenolic ring by one or more alkyl groups, to the corresponding optionally substituted 2-hydroxybenzylidenearylamine which (2) is hydrolyzed to the corresponding optionally substituted o-hydroxybenzaldehyde.

10 Claims, No Drawings

PROCESS FOR PREPARING O-HYDROXYARYLALDEHYDES

This invention relates to an improved process for the manufacture of hydroxyaryl aldehydes.

o-hydroxyarylaldehydes are useful as for example perfumery and flavouring agents and as intermediates for the corresponding oximes which in the case of alkyl substituted o-hydroxyarylaldehydes are of value in hydrometallurgical extraction processes.

According to the invention there is provided a process for the manufacture of o-hydroxyarylaldehydes which comprises the steps of (1) oxidising a 2-arylaminomethylphenol, optionally substituted in the phenolic ring by one or more alkyl groups, to the corresponding optionally substituted 2-hydroxybenzylidenearylamine which (2) is hydrolysed to the corresponding optionally substituted o-hydroxybenzaldehyde.

The first, oxidation, step may be carried out by aerial oxidation but it is preferred to use conventional oxidising agents which are salts of metals in one of their higher valency states, for example ferric sulphate, cupric sulphate, manganic salts form in situ form manganese dioxide and sulphuric acid, and complex salts derived from these, for example potassium ferricyanide, and oxidising acids such as nitric acid and salts of oxidising acids, for example ammonium persulphate and potassium permanganate.

It is preferred to carry out the oxidation in aqueous media under acid conditions, for example in dilute sulphuric acid. Preferred temperatures for the oxidation are from 70° C to 100° C, but temperatures outside this range, for example between 40° and 70° C., can be used if desired.

The amount of oxidising agent is desirably such as to give at least one g. atom of oxygen per g. mol of 2-arylaminomethylphenol.

If desired the oxidation step may be carried out in presence of a water-immiscible solvent, such as a hydrocarbon e.g. cyclohexane. In these cases wherein the 2-arylaminomethylphenol has been prepared in presence of such a solvent this enables use of the 2-arylaminomethylphenol in the solvent without isolation.

The second, hydrolysis, step may be carried out by heating with aqueous acid of concentration preferably greater than in the first step, for example sulphuric acid of strength above 1N. Other strong acids at comparable concentrations in water may be used.

The preferred hydrolysis temperature is between 20° C and 100° C but temperatures above 100° C under pressure can be used.

The amount of acid is conveniently between the range of 1 to 6 mol. for every mol. of alkyl phenol from which the 2-arylamino methylphenol was prepared. Use of less or more dilute acid may lead to incomplete hydrolysis unless unduly long reaction times are employed.

The hydrolysis step, like the oxidation step, may be carried out in presence of a water-immiscible solvent such as a hydrocarbon e.g. cyclohexane, which in appropriate cases permits use of the reaction mixture from step 1 in step 2 without any separation procedure.

In cases where water-immiscible solvent is present and the hydrolysis step is slow it may be desirable to carry out the step, or complete the step, by heating with the acid in presence also of a water-miscible solvent, such as 2-ethoxyethanol.

Steps 1 and 2 may be combined into one operation by using acid of a concentration necessary for complete hydrolysis, for example 1-12N sulphuric acid, the 2-hydroxybenzylidenearylamine being hydrolysed as it is formed to the o-hydroxybenzaldehyde.

The product may conveniently be isolated by extraction of the reaction mixture after the hydrolysis step with a water-immiscible solvent and then removing the solvent from the extract by for example heating under reduced pressure. This procedure may use the solvent, such as cyclohexane which was present in step 2.

If it is intended to use the o-hydroxybenzaldehyde to prepare the corresponding oxime it is often convenient to carry this out without isolation of the o-hydroxybenzaldehyde, by reaction of the crude product with hydroxylamine.

The starting material for step 1, the 2-arylaminomethylphenol, may be readily prepared by reacting a phenol or alkylphenol having a free ortho-position, the arylamine, and formaldehyde or a formaldehyde precursor or generator such as paraform, 1,3,5-trioxan or the formaldehyde/bisulphate compound or methylal. The reaction may be carried out by heating the three reactants alone or in a solvent. The solvent may be for example an alcohol such as methanol, ethanol or isopropanol or an aromatic solvent such as toluene, or acetic acid but it is preferred to use an aqueous medium. If desired a heterogeneous solvent system consisting of an aqueous medium and a water-insoluble solvent such as a hydrocarbon e.g. cyclohexane may be used.

It is preferred to use neutral or mildly alkaline conditions and buffers such as sodium acetate or sodium carbonate but an acid medium can be used especially if the formaldehyde is used in the form of methylal. If desired the arylamine may be added in the form of a salt such as the sulphate in which case it is preferably to add an acid-binding agent such as sodium carbonate or sodium hydroxide to liberate the free arylamine.

Convenient temperatures for preparing the 2-arylaminomethylphenol are from 20° C to 100° C.

Use of too high a temperature or too long a reaction time may lead to undesirable formation of bis-(arylaminomethyl)phenols.

Normally one molar proportion of arylamine or slightly less say 0.8 mol and of formaldehyde with respect to the phenol is required and it is preferred to use an excess, conveniently up to 100%, of each. The molar amounts of arylamine to formaldehyde are conveniently substantially the same but some excess of either can be tolerated and in some cases it may be desirable to use an excess, up to 100%, of formaldehyde. Under these latter conditions the 2-arylaminomethylphenol is at least in part converted by the excess formaldehyde into the derived 3,4-dihydro-3-aryl-1,3,2H-benzoxazine and the formation of bis(arylaminomethy)phenols is reduced. The 3,4-dihydro-3-aryl-1,3,2H-benzoxazines are however converted into the corresponding 2-arylaminomethylphenols under the conditions of the first step of the process and may therefore be used in place of 2-arylaminomethylphenols as precursors therefor in the first, oxidation, step of the process. The use of these oxazines as replacements at least in part of 2-arylaminomethylphenols in this process is a further feature of the invention.

As examples of suitable arylamines there may be mentioned aniline, o-anisidine, p-toluidine, p-chloroaniline, 4,4'-diaminodiphenylmethane, p-phenylenediamine and N,N-dialkyl-p-phenylenediamines. The hydrolysis step is easier when one of the p-phenylenediamines is used, but for economic reasons it is usually preferable to use a monoamine, especially a para-substituted monoamine, for example p-toluidine.

Phenol itself or any alkylphenol having a free o-position may be used but the invention is of particular value with p-alkylphenols to provide 5-alkyl-2-hydroxybenzaldehydes. As p-alkylphenols there may be mentioned for example p-cresol and p-tert.-butylphenol but especially p-alkylphenols in which the alkyl group contains 5 or more carbon atoms and preferably 7 to 12 from phenols by alkylation with olefins and olefin mixtures such as mixtures of heptenes or propylene trimer. The oximes from the p-alkyl-2-hydroxybenzaldehydes derived from these alkylphenols are of value in hydrometallurgical extraction processes. The p-alkyl-2-hydroxy benzaldehydes may contain small amounts of the p-alkylphenols but these do not have any deleterious effects in such extraction processes and further purification is unnecessary for such end-uses.

In the case of alkylphenols wherein the alkyl group contains 5 or more carbon atoms the 2-arylaminomethyl-4-alkylphenols, the derived 3,4-dihydro-3-aryl-1,3,2H-benzoxazines, and the alkyl (2-hydroxybenzylidenearylamines are novel compounds and these, and the separate reaction steps for their manufacture and the hydrolysis step leading to the alkyl-2-hydroxybenzaldehydes, are also features of the invention.

The invention is illustrated but not limited by the following examples in which all parts and percentages are by weight unless otherwise stated.

EXAMPLE 1

4-Nonylphenol (commercial material obtained by alkylation of phenol with propylene trimer) (11 parts), 4-amino-N,N-diethylaniline sulphate (13.1 parts), formaldehyde 37% solution (4 parts), and cyclohexane (35 parts), were added to a stirred glass vessel and a solution of sodium carbonate anhydrous (10.6 parts) added over 15 minutes. The mixture was heated to a temperature of 40° C and held at 38°–42° C. for 21 hours. The cyclohexane layer consisting of a solution of the Mannich base 2-(4-diethylamino-phenylmethyl)-4-nonyl phenol was separated off, washed with water (50 parts). and charged to a flask together with a solution of sulphuric acid (5.6 parts) in water (50 parts). A solution of anhydrous ferric sulphate (20 parts) in water (20 parts) was added, the mixture heated with stirring to 30° C., held at this temperature for 1 hour, then heated to 60° C. and held for 2 hours. Sulphuric acid (5 parts) in water (10 parts) was added, the temperature being maintained at 60° C. for a further ½ hour. The mixture was cooled to room temperature, the cyclohexane layer separated off, washed acid free with water and finally concentrated by vacuum distillation at 80° C to give 11.8 parts of a brown oil. This was shown by thin layer chromatography followed by Ultra Violet absorption at 335 nm to contain 5.8 parts of 5-nonylsalicylaldehyde, corresponding to a yield of 46.8% theory based on the initial charge of 4-nonylphenol. Gas-liquid chromatographic analysis of the oil showed that it contained 2.5 parts of 4-nonylphenol. The yield of 5-nonylsalicylaldehyde was therefore 60.5% of theory, based on the amount of 4-nonyl phenol consumed in the reaction.

EXAMPLE 2

Water (80 parts) was charged to a stirred glass vessel, followed by sodium sulphite anhydrous (13.86 parts), paraformaldehyde (3.3 parts), sodium bicarbonate (9.24 parts), and 4-toluidine (11.8 parts). The mixture was stirred for 5 minutes at 25° C, after which 4-nonylphenol (22 parts) was added, and the temperature raised to 70° C. over ¾ hour. The temperature was maintained at 66°–74° C for 2 hours and then lowered to 24° C when cyclohexane (71 parts) was added. The cyclohexane solution of the Mannich base 2-(4-methylphenylamino methyl)-4-nonylphenol was separated off and the aqueous portion re-extracted with cyclohexane (16 parts). The cyclohexane solutions were combined, filtered through Hyflo-Supercel and the filtrates charged to a flask containing anhydrous ferric sulphate (80 parts) dissolved in water (80 parts) and a solution of sulphuric acid (22.4 parts) in water (200 parts). The mixture was heated at 68°–72° C. for 21 hours when sulphuric acid (20 parts) in water (40 parts) was added. It was then cooled, the cyclohexane layer separated off and heated with 2-ethoxyethanol (94 parts) in 6N sulphuric acid (61 parts) at 70° C for 2 hours. Water (100 parts) was added, the cyclohexane layer separated off, washed with water until acid free and evaporated down under vacuum at 80° C. A brown oil (24.5 parts) remained which was shown by thin layer chromatography and Ultra Violet absorption at 335 nm to contain 12.5 parts of 5-nonyl salicylaldehyde, corresponding to a yield of 50.4% theory, based on the initial charge of 4-nonylphenol. Gas-liquid chromatographic analysis of the oil showed that it contained 5.9 parts of 4-nonylphenol. The yield of 5-nonylsalicylaldehyde was therefore 68.6% of theory, based on the amount of 4-nonylphenol consumed in the reaction.

EXAMPLE 3

A mixture of 4-toluidine (16.05 parts), 4-nonylphenol (22 parts), methanol (35 parts), methylal (11.4 parts) and water (16.5 parts) was stirred at room temperature until a pale yellow solution was obtained. Sulphuric acid (95% strength, 32.2 parts) was added over 10 minutes, the temperature not exceeding 35° C. The mixture was heated to 50° C. and held at 49°–51° C. for 23 hours. Xylene (45 parts) was added and the mixture stirred and cooled to 30° C. when a solution of sodium hydroxide (40% strength, 60.9 parts) in water (45 parts) was added with cooling over ½ hour. The pH of the aqueous layer was now 7–8. The xylene layer containing the Mannich base 2-(4-methylphenylaminomethyl)-4-nonylphenol was separated, washed with water (3×50 parts) and then added to a solution of ferric sulphate anhydrous (80 parts) and sulphuric acid (95% strength, 22.4 parts) in water (200 parts). The mixture was heated at 92°–94° C. for 20 hours and then cooled; the xylene solution separated off and washed with water (50 parts). The xylene solution was then refluxed at 93°–95° C. for 2½ hours with a solution of sulphuric acid (95% strength, 20.4 parts) in water (56 parts), then cooled to 50° C., separated and washed acid free with water. The xylene solution was evaporated under vacuum to give a brown oil (27.7 parts) which was shown by thin layer chromatography and ultra violet absorption at 335 nm to contain 10.4 parts of 5-nonylsalicylaldehyde, corresponding to a yield of 42.0% theory, based on the initial charge of 4-nonylphenol. Gas-liquid chromatographic analysis of the oil showed that it contained 7.5 parts of 4-nonylphenol. The yield of 5-nonylsalicylaldehyde was therefore 63.9% of theory, based on the amount of 4-nonylphenol consumed in the reaction.

EXAMPLE 4

A mixture of 4-nonylphenol (22 parts), 2-methoxyaniline (13.5 parts), formalin 27% solution (12.2 parts) and sodium carbonate anhydrous (21.2 parts) was stirred in cyclohexane (81 parts) and water (170 parts) for 68 hours at 20° C. The organic layer, consisting of a cyclohexane solution of the Mannich base 2-(2-methoxyphenylaminomethyl)-4-nonylphenol was separated off, washed with water and added to a stirred solution of ferric sulphate anhydrous (44 parts) and sulphuric acid (11.2 parts) in water (144 parts). The mixture was heated to 30° C, held for 1 hour at this temperature and then heated to 70° C and held for 3 hours. A further amount of sulphuric acid (10 parts) in water (20 parts) was added, and heating continued for a further ½ hour. The mixture was then cooled, ethyl acetate (90 parts) added and the organic layer separated, washed with water until acid free and then evaporated down to yield a brown oil (17 parts) which was shown by thin layer chromatography, followed by ultraviolet absorption at 335 nm to contain 11.1 parts of 5-nonylsalicylaldehyde, corresponding to a yield of 44.7% of theory, based on the initial charge of 4-nonylphenol. Gas-liquid chromatographic analysis of the oil showed that it contained 2.5 parts of 4-nonylphenol. The yield of 5-nonylsalicylaldehyde was therefore 50.5% of theory based on the amount of 4-nonylphenol consumed in the reaction.

EXAMPLE 5

A stirred mixture of 4-nonylphenol (44 parts), 4-toluidine (21.4 parts), paraformaldehyde (6.0 parts) in toluene (54 parts) was heated to 40° ± 1° C under a vacuum of 30–40 mm.Hg. These reaction conditions were maintained for a total of 7 hours whilst water (3.6 parts) was removed by azeotropic distillation. The resulting toluene solution of the Mannich base 2-(4-methylphenylaminomethyl)-4-nonylphenol was washed with water (100 parts) and then heated with a solution of ferric sulphate anhydrous (160 parts) and sulphuric acid (3.8 parts) in water (213 parts) for 21 hours at 87° ± 1° C. The toluene solution was separated off and heated for a further 6 hours with a solution of sulphuric acid (38.8 parts) in water (112 parts) at 87° ± 1° C. The toluene solution was separated off, washed acid free with water and evaporated down to yield 54 parts of a brown oil which was shown by thin layer chromatography, followed by ultra violet absorption at 335 nm to contain 28.3 parts of 5-nonylsalicylaldehyde, corresponding to a yield of 57.1% of theory, based on the initial charge of 4-nonylphenol. The oil was analysed by gas-liquid chromatography and found to contain 11.6 parts of 4-nonylphenol. The yield of 5-nonylsalicylaldehyde was therefore 77.5% of theory, based on the amount of 4-nonylphenol consumed in the reaction.

EXAMPLE 6

A mixture of 4-nonylphenol (22 parts), 4-toluidine (9.6 parts), paraformaldehyde (2.7 parts), sodium carbonate anhydrous (1.1 parts) and water (8.2 parts) was heated with stirring to 42° ± 2° C and held at this temperature for 2½ hours. Toluene (22.5 parts) was then added and heating continued for a further ¼ hour. The toluene solution of the Mannich base 2-(4-methylphenylaminomethyl)-4-nonylphenol was then separated off and charged to a stirred glass vessel containing 10 parts of a solution of sulphuric acid of strength 0.2N. The mixture was heated to 49° C and a solution of ammonium persulphate (22.8 parts) in water (41 parts) added over 1 hour whilst maintaining the temperature at 55°±5° C. The temperature was then maintained at 50°±1° C for 1½ hours. The toluene solution was then separated off and heated for 6 hours at 85° ± 1° C with a solution of sulphuric acid (18.5 parts) in water (37.5 parts). The toluene solution was then evaporated down to give a dark brown oil (28.8 parts) which by analysis as previously described was found to contain 8.8 parts of 5-nonylsalicylaldehyde, corresponding to a yield of 35.5% of theory based on the initial charge of 4-nonylphenol.

EXAMPLE 7

A mixture of commercial 4-heptylphenol (230.4 parts), 4-toluidine (115.6 parts), paraformaldehyde (32.4 parts), sodium carbonate anhydrous (12.7 parts), in water (98 parts) was heated with stirring at 42° ± 2° C for 2¼ hours. Toluene (270 parts) was added and the mixture stirred for a further ¼ hour. The toluene layer, containing the Mannich base 2-(4-methylphenylaminomethyl)-4-heptylphenol was separated off, washed with water (100 parts), and then added to a stirred solution of ferric sulphate 42% w/w strength (1371 parts). The mixture was heated to 86° ± 2° C and held at this temperature for 18 hours. The toluene layer was separated off and heated for a further 6 hours with a solution of sulphuric acid (222 parts) in water (450 parts). The organic layer was then separated, washed acid free with water and evaporated down to give a brown oil (268.1 parts). This was analysed by thin layer chromatography, followed by ultraviolet absorption at 335 nm and found to contain 146.4 parts of 5-heptylsalicylaldehyde, corresponding to a yield of 55.5% of theory based on the initial charge of 4-heptylphenol. Gas-liquid chromatographic analysis of the oil showed that it contained 68.4 parts of 4-heptylphenol. The yield of 5-heptylsalicylaldehyde was therefore 78.9% of theory based on the amount of 4-heptylphenol consumed in the reaction.

EXAMPLE 8

A mixture of 4-tert.octylphenol (20.6 parts), 4-toluidine (9.6 parts), paraformaldehyde (2.7 parts), sodium carbonate anhydrous (1.1 parts), toluene (22.5 parts) and water (8 parts) was heated to 42° ± 2° C with stirring, and maintained at this temperature for 3 hours. The resulting toluene solution of the Mannich base 2-(4-methylphenylaminomethyl)-4-tert.octylphenol was separated off, washed with water (10 parts) and added to a solution of ferric sulphate anhydrous (60 parts) and sulphuric acid (1.9 parts) in water (106.5 parts). The mixture was heated with stirring at 86° ± 1° C for 17 hours. The toluene layer was separated off and heated for a further 6 hours in a solution of sulphuric acid (18.5 parts) in water (37.5 parts). The organic layer was then separated, washed acid free with water, and then evaporated to a brown oil (25.5 parts), which was shown to contain 11.9 parts of 5-tert.octylsalicylaldehyde by thin layer chromatography followed by ultraviolet absorption. This corresponds to a yield of 51% of theory, based on the initial charge of 4-tert.octylphenol.

EXAMPLE 9

In an experiment carried out as in Example 8 but using 4-tert. amylphenol (16.4 parts) to give the Mannich base 2-(4-methylphenylaminomethyl)-4-tert.amylphenol, there was finally obtained an oil (20.9 parts) which by thin layer chromatographic/U.V. analysis was found to contain 12.8 parts of 5-tert.amyl salicylaldehyde, corresponding to a yield of 66.7% of theory, based on the initial charge of 4-tert.amylphenol.

EXAMPLE 10

A stirred mixture of 4-nonylphenol (88 parts), 4-toluidine (47.1 parts), and paraformaldehyde (26 parts) in water (32 parts) was heated at 100° C for 12 hours. Samples of the reaction mixttaken during the reaction and examined by thin layer chromatographic analysis, indicated that the major reaction component was 6-nonyl-3-p-tolyl-3,4-dihydro-2H, 1,3-benzoxazine. Xylene (90 parts) was then added and the mixture stirred for a further ¼ hour. The xylene solution of the dihydrobenzoxazine was separated off and added to a solution of ferric sulphate anhydrous (252 parts) and sulphuric acid (80 parts) in water (270 parts). The mixture was heated to 98° C and held at 98° ± 1° C for 20 hours. The mixture was cooled and filtered and the xylene layer separated off, and then stirred with a solution of sulphuric acid (117.6 parts) in water (200 parts) at 85° C for 3 hours. The xylene layer was then separated off, washed acid free with water and evaporated down to yield 104 parts of a brown oil which was shown by thin layer chromatography, followed by ultraviolet absorption at 335 nm, to contain 55.6 parts of 5-nonylsalicylaldehyde, corresponding to a yield of 56.0% of theory, based on the initial charge of 4-nonylphenol. Gas liquid chromatographic analysis of the oil showed that it contained only traces of 4-nonylphenol.

The above Example illustrates the process of the invention using a dihydro-benzoxazine as starting material, the dihydro-benzoxazine acting as a precursor for 2-(4-methylphenylaminomethyl)-4-nonylphenol which is formed in situ from the dihydro-benzoxazine.

What we claim is:

1. A process for the manufacture of an o-hydroxyarylaldehyde of the formula:

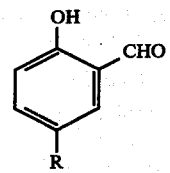

wherein R is an alkyl group of from 7 to 12 carbon atoms which comprises the steps of (1) oxidizing a 2-arylaminomethyl phenol of the formula:

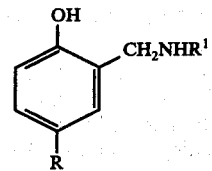

wherein —NHR$^1$ is the residue of an aromatic amine selected from aniline, p-toluidine, o-anisidine and p-chloroaniline with ferric sulphate or ammonium persulphate under acid conditions in aqueous medium at 40° to 100° C. to the corresponding 2-hydroxybenzylidenearylamine and (2) hydrolyzing said amine to the o-hydroxyarylaldehyde by heating with aqueous acid.

2. A process as claimed in claim 1 wherein the oxidation temperature is 70° to 100° C.

3. A process as claimed in claim 1 wherein sufficient oxidising agent is used in the oxidation step to give at least one gram atom of oxygen per gram mol of 2-arylaminomethylphenol.

4. A process as claimed in claim 1 wherein a water-immiscible solvent is present in the oxidation step.

5. A process as claimed in claim 1 wherein the second or hydrolysis step is carried out by heating with aqueous acid of concentration greater than that in the first step.

6. A process as claimed in claim 1 wherein hydrolysis is carried out at a temperature of 20° to 100° C.

7. A process as claimed in claim 1 wherein the amount of acid used in the hydrolysis is from 1 to 6 mol per mol of alkylphenol from which the 2-arylaminomethylphenol was prepared.

8. A process as claimed in claim 1 wherein the hydrolysis step is carried out in the presence of a water-immiscible solvent.

9. A process as claimed in claim 1 wherein steps 1 and 2 are combined in one operation using acid of a concentration necessary for complete hydrolysis of the o-hydroxybenzaldehyde.

10. A process as claimed in claim 1 wherein the 2-arylaminomethylphenol used as starting material is produced in situ in the reaction mixture from a 3,4-dihydro-3-aryl-1,3,2H-benzoxazine.

* * * * *